United States Patent
Carpenter et al.

(10) Patent No.: US 9,434,596 B2
(45) Date of Patent: Sep. 6, 2016

(54) BEVERAGE DISPENSING SYSTEM

(71) Applicant: The Coca-Cola Company, Atlanta, GA (US)

(72) Inventors: Gregg Carpenter, Marietta, GA (US); David R. Newman, Jr., Atlanta, GA (US); Nilang Patel, Mableton, GA (US); Paul A. Phillips, Marietta, GA (US); Arthur G. Rudick, Atlanta, GA (US); Lawrence B. Ziesel, Woodstock, GA (US)

(73) Assignee: The Coca-Cola Company, Atlanta, GA (US)

( * ) Notice: Subject to any disclaimer, the term of this patent is extended or adjusted under 35 U.S.C. 154(b) by 0 days.

(21) Appl. No.: 14/317,821

(22) Filed: Jun. 27, 2014

(65) Prior Publication Data

US 2014/0374438 A1    Dec. 25, 2014

Related U.S. Application Data

(63) Continuation of application No. 13/897,518, filed on May 20, 2013, now Pat. No. 8,807,393, which is a continuation of application No. 13/401,938, filed on Feb. 22, 2012, now Pat. No. 8,453,879, which is a continuation of application No. 13/036,081, filed on Feb. 28, 2011, now Pat. No. 8,162,181, which is a continuation of application No. 12/784,730, filed on May 21, 2010, now Pat. No. 7,913,879, which is a continuation of application No. 11/276,550, filed on Mar. 6, 2006, now Pat. No. 7,757,896.

(51) Int. Cl.
| | | |
|---|---|---|
| *B67D 1/00* | (2006.01) | |
| *B67D 1/08* | (2006.01) | |
| *B67D 7/00* | (2010.01) | |
| *B67D 7/74* | (2010.01) | |
| *B67D 7/78* | (2010.01) | |
| *G07F 13/06* | (2006.01) | |
| *G07F 11/00* | (2006.01) | |

(52) U.S. Cl.
CPC .......... *B67D 1/0888* (2013.01); *B67D 1/0035* (2013.01); *B67D 1/0051* (2013.01); *B67D 1/0085* (2013.01); *B67D 1/0021* (2013.01); *B67D 1/0027* (2013.01); *B67D 1/0032* (2013.01); *B67D 1/0034* (2013.01); *B67D 1/0041* (2013.01); *B67D 1/0044* (2013.01); *B67D 2210/00089* (2013.01); *G07F 11/002* (2013.01); *G07F 13/065* (2013.01)

(58) Field of Classification Search
CPC  B67D 1/0021; B67D 1/0044; B67D 1/0051; B67D 1/0888; B67D 1/0035; B67D 1/0085; B67D 1/0027; B67D 1/0032; B67D 1/0034; B67D 1/0041; B67D 2210/00089; B67D 1/1234; A61J 15/008; A61B 5/0002; G07F 13/065; G07F 11/002; G06F 3/0482
See application file for complete search history.

(56) References Cited

U.S. PATENT DOCUMENTS 3,822,056 A * 7/1974 Hawes et al. ............... 366/114
5,803,320 A * 9/1998 Cutting et al. .............. 222/641

(Continued)

*Primary Examiner* — Frederick C Nicolas
(74) *Attorney, Agent, or Firm* — Sutherland Asbill & Brennan LLP

(57) ABSTRACT

The present application describes a product dispenser. The product dispenser may include at least one macro-ingredient source, at least one micro-ingredient source positioned about the dispenser, a diluent source, a dispensing valve, a number of pumps or metering devices, and a user interface. The user interface receives a request for a product type and instructs the pumps or metering devices to dispense a predetermined type and ratio of macro-ingredients, micro-ingredients, and diluent to the dispensing valve for a predetermined flow rate.

19 Claims, 2 Drawing Sheets

(56) References Cited

U.S. PATENT DOCUMENTS

| | | | |
|---|---|---|---|
| 6,182,555 B1* | 2/2001 | Scheer et al. | 99/290 |
| 6,975,910 B1* | 12/2005 | Brown et al. | 700/90 |
| 7,756,604 B1* | 7/2010 | Davis et al. | 700/240 |
| 7,762,181 B2* | 7/2010 | Boland et al. | 99/322 |
| 8,490,829 B2* | 7/2013 | Deo | B67D 1/0027 222/129.4 |
| 2002/0107610 A1* | 8/2002 | Kaehler et al. | 700/232 |
| 2003/0057226 A1* | 3/2003 | Long | 221/92 |
| 2004/0254837 A1* | 12/2004 | Roshkoff | 705/14 |
| 2005/0133420 A1* | 6/2005 | Rinker | A23L 1/30 210/143 |
| 2005/0199646 A1* | 9/2005 | Moy | B67D 1/0021 222/1 |
| 2006/0173260 A1* | 8/2006 | Gaoni | A61B 5/0002 600/365 |
| 2006/0231109 A1* | 10/2006 | Howell | A61B 5/6887 128/898 |
| 2007/0073557 A1* | 3/2007 | Abramson | G06Q 20/18 705/2 |
| 2007/0114244 A1* | 5/2007 | Gatipon et al. | 222/129.1 |

* cited by examiner

BEVERAGE DISPENSING SYSTEM

RELATED APPLICATIONS

This application is a continuation of U.S. application Ser. No. 13/897,518, filed May 20, 2013; which is a continuation of U.S. application Ser. No. 13/401,938, filed Feb. 22, 2012, now U.S. Pat. No. 8,453,879, issued Jun. 4, 2013; which is a continuation of U.S. application Ser. No. 13/036,081, filed Feb. 28, 2011, now U.S. Pat. No. 8,162,181, issued Apr. 24, 2012; which is a continuation of U.S. application Ser. No. 12/784,730, filed on May 21, 2010, now U.S. Pat. No. 7,913,879, issued on Mar. 29, 2011; which is a continuation of U.S. application Ser. No. 11/276,550, filed Mar. 6, 2006, now U.S. Pat. No. 7,757,896, issued on Jul. 20, 2010. U.S. Pat. Nos. 7,757,896, 7,913,879, 8,162,181, and 8,453,879, and U.S. application Ser. No. 13/897,518 are incorporated herein by reference in their entireties.

TECHNICAL FIELD

The present application relates generally to beverage dispensing systems and more particularly relates to a beverage dispenser for providing a number of different beverage alternatives.

BACKGROUND OF THE INVENTION

Commonly owned U.S. Pat. No. 4,753,370 concerns a "Tri-Mix Sugar-Based Dispensing System." This patent describes a beverage dispensing system that separates the highly concentrated flavoring from the sweetener and the diluent. This separation allows for the creation of numerous beverage options using several flavor modules and one universal sweetener. One of the objectives of the patent is to allow the beverage dispenser to provide as many beverages as may be available on the market in pre-packaged bottles or cans. U.S. Pat. No. 4,753,370 is incorporated herein by reference.

These separation techniques have continued to be refined and improved. As is shown in commonly owned U.S. patent application Ser. No. 11/276,553, entitled "Methods and Apparatuses for Making Compositions Comprising an Acid and an Acid Degradable Component and/or Compositions Comprising a Plurality of Selectable Components", the acid and non-acid components of the non-sweetened concentrate also may be separated. This separation allows for a prolonged shelf life and also enables further concentration of the flavor components. U.S. patent application Ser. No. 11/276,553 is incorporated herein by reference.

Beverage dispensers historically have worked by combining a diluent (such as water) with a beverage base. These beverage bases usually have a reconstitution ratio of about 3:1 to 6:1. The beverage bases usually come in large containers that require large amounts of storage space and may need to be refrigerated. Theses requirements often necessitate the need to store these containers far from the actual dispenser and to run long lines from the containers to the dispenser.

Given the improvements in shelf life and concentration described above, there is a desire for a beverage dispenser that can produce even more and different types of beverages while using a smaller footprint. This can be accomplished by breaking down the traditional beverage bases into constituent parts at much higher reconstitution ratios. These parts can then be stored in much smaller packages and stored closer to, adjacent to, or within the beverage dispenser itself.

The beverage dispenser preferably can give the consumer multiple beverage options such that the consumer has the ability to customize his or her beverage as desired.

SUMMARY OF THE INVENTION

The present application thus describes a product dispenser. The product dispenser may include at least one macro-ingredient source, at least one micro-ingredient source positioned about the dispenser, a diluent source, a dispensing valve, a number of pumps or metering devices, and a user interface. The user interface receives a request for a product type and instructs the pumps or metering devices to dispense a predetermined type and ratio of macro-ingredients, micro-ingredients, and diluent to the dispensing valve for a predetermined flow rate.

The user interface may include a control device. The control device instructs the number of pumps or metering devices to dispense a predetermined type and ratio of macro-ingredients, micro-ingredients, and diluent to the dispensing valve for the predetermined flow rate.

The macro-ingredient source may include a macro-ingredient with a reconstitution ratio of about 3:1 to about 6:1. The macro-ingredient source may include sugar syrups, HFCS (High Fructose Corn Syrup), and juice concentrates. The micro-ingredient source may include a micro-ingredient with a reconstitution ratio of about 10:1 or higher. The micro-ingredient source may include natural and artificial flavors, natural and artificial colors, artificial sweeteners, vitamins, minerals, herbal extracts, nutraceuticals, pharmaceuticals, and acid and non-acid components of flavoring.

The diluent source and the macro-ingredient source each may be in communication with one of the pumps. The micro-ingredient source may be in communication with one of the metering devices. The pumps or metering devices may include a positive displacement pump.

The dispensing valve may include a multi-flavor valve. The dispensing valve may include a flow director in communication with the macro-ingredient source and the diluent source. The dispensing valve may include a tertiary flow assembly in communication with the micro-ingredient source.

The user interface may include a number of product selections, a number of additive selections, a number of intensity selections, nutritional information, and a consumer data system. The consumer data system may include one or more biometric sensors. The product type may be a custom product or a branded product.

The present application further describes a mixer for producing a number of product types. The mixer may include a number of ingredient sources positioned about the mixer with ingredients having reconstitution ratios higher than about ten to one, a diluent source, a number of pumps or metering devices, and a user interface. The user interface receives a request for one of the product types and instructs the pumps or metering devices to dispense a predetermined type and ratio of ingredients and diluent for a predetermined flow rate.

The present application further describes a beverage dispenser for producing a plurality of beverages. The beverage dispenser may include a number of ingredient sources positioned about the dispenser having ingredients with reconstitution ratios higher than about ten to one, a diluent source, and a number of pumps or metering devices in communication with the ingredient sources and the diluent source.

The present application further describes a product dispenser. The product dispenser may include at least one macro-ingredient source, at least one micro-ingredient source positioned about the dispenser, a diluent source, a dispensing valve, a number of pumps or metering devices, and a user interface. The user interface receives a request for a branded beverage and instructs the pumps or metering devices to dispense a predetermined type and ratio of macro-ingredients, micro-ingredients, and diluent to the dispensing valve.

These and other features of the present application will become apparent to one of ordinary skill in the art upon review of the following detailed description of the invention when taken in conjunction with the several drawings and the appended claims.

DETAILED DESCRIPTION

Figure 1:
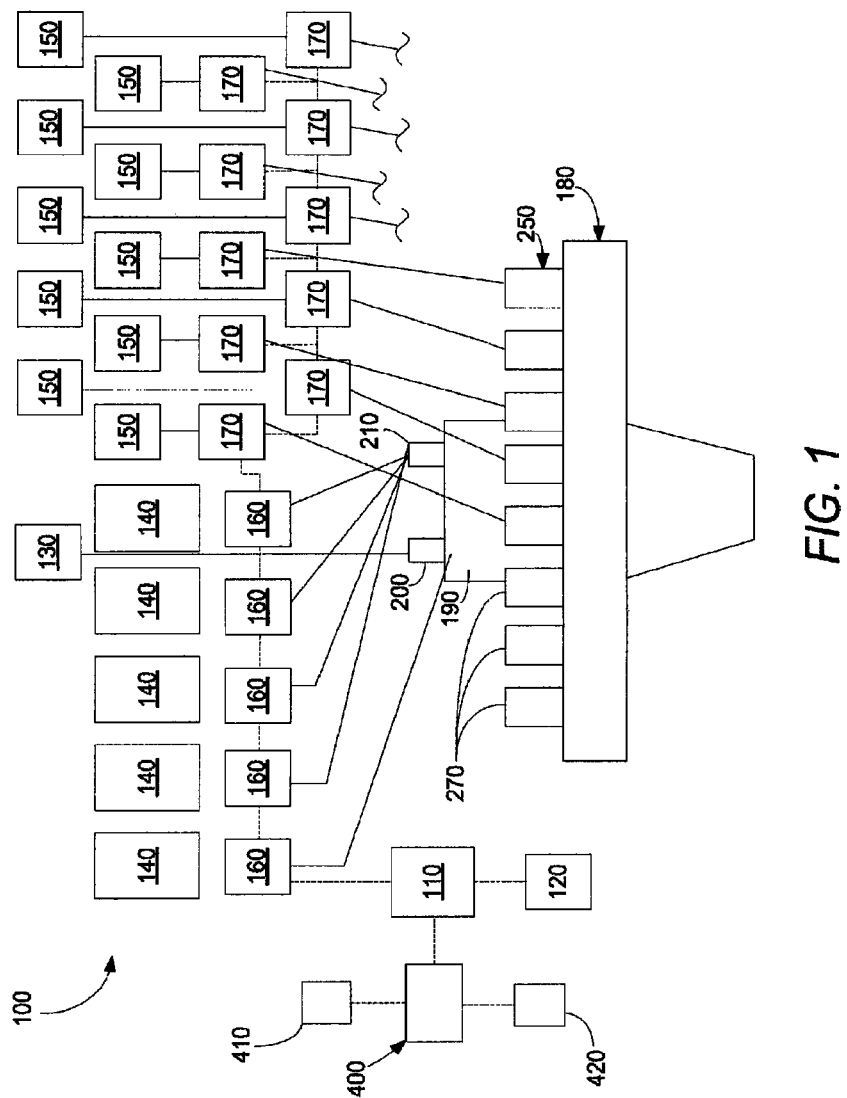
FIG. 1 is a schematic view of a beverage dispenser as is described herein.

Referring now to the drawings, in which like numerals indicate like elements throughout the several views, FIG. 1 shows a beverage dispenser 100 as is described herein. A user interface 110 may control all of the functional aspects of the beverage dispenser 100. A consumer may select and/or create numerous types of beverages, blends, and additives using the user interface 110. A control device 120 may support the user interface 110. The control device 120 may be a conventional microcomputer or a similar type of device. The control device 120 may be internal to or remote from the beverage dispenser 100.

The beverage dispenser 100 may use any number of different ingredients. In this example, several different types of ingredients may be used: water (plain and/or carbonated) from a water source 130; macro-ingredients from a number of macro-ingredient sources 140; and micro-ingredients from a number of micro-ingredient sources 150. Any number or combinations of sources 130, 140, 150 may be used herein. For example, it may not be necessary to have a macro-ingredient source, e.g., HFCS, which is difficult to pump at high reconstitution ratios, may not be used. As such, only a diluent and a micro-ingredient source may be required.

The water from the water source 130 may or may not be refrigerated. Other types of diluents may be used herein. A conventional carbonator or a similar type of device may be used to produce carbonated water as desired. The amount of carbonation may be varied.

Generally described, the macro-ingredients may have reconstitution ratios in the range of about 3:1 to about 6:1. The viscosities of the macro-ingredients typically range from about 100 or higher. Macro-ingredients may include sugar syrup, HFCS (High Fructose Corn Syrup), juice concentrates, and similar types of fluids. Similarly, a macro-ingredient base product may include sweetener, acid, and other common components. The syrups, sweeteners, and base products generally can be stored in a conventional bag-in-box container remote from the dispenser 100. The macro-ingredients also may be positioned within the beverage dispenser 100 itself. Any type of container may be used herein. The macro-ingredients may or may not need to be refrigerated.

The micro-ingredients may have a reconstitution ratio ranging from about ten to one (10:1), twenty to one (20:1), thirty to one (30:1), or higher. Specifically, many micro-ingredients may be in the range of fifty to one (50:1) to three hundred to one (300:1). The viscosities of the micro-ingredients typically range from about 1 to about 100 centipoise or so. Examples of micro-ingredients include natural and artificial flavors; flavor additives; natural and artificial colors; artificial sweeteners (high potency or otherwise); additives for controlling tartness, e.g., citric acid, potassium citrate; functional additives such as vitamins, minerals, herbal extracts; nutraceuticals; and over-the-counter (or otherwise) medicines such as acetaminophen and similar types of materials. As described above, the acid and non-acid components of the non-sweetened concentrate also may be separated and stored individually. The micro-ingredients may be liquid, powder (solid), or gaseous form and/or combinations thereof. The micro-ingredients may or may not require refrigeration. Non-beverage substances such as paints, dyes, oils, cosmetics, etc., also may be used. Various types of alcohols may be used as micro or macro-ingredients.

Preferably, the micro-ingredients and the micro-ingredient sources 150 may be positioned within or about the beverage dispenser 100 itself as opposed to being remotely positioned in conventional bag in box containers or otherwise. By being positioned about the dispenser, we mean that the micro-ingredient sources 150 are positioned in close proximity to the dispenser 100 such as adjacent thereto, underneath, or in other near by positions. Any other type of storage arrangements may be used. Any type of container may be used herein.

The water source 130, the macro-ingredient sources 140, and the micro-ingredient sources 150 each may be in communication with a pump 160 or a metering device 170. The control device 120 may control the pumps 160 and metering devices 170. Generally described, the water source 130 and the macro-ingredient sources 140 each may be in communication with one of the pumps 160. The pump 160 may be a conventional solenoid pump or a similar type of device.

The micro-ingredient sources 150 each may be in communication with one of the metering device 170. The metering device 170 may be a positive displacement pump or a similar type of device. Such a positive displacement pump provides portion control for the more highly concentrated micro-ingredients. An example of the operation of a positive displacement pump is shown in commonly owned U.S. Pat. No. 7,740,152, entitled "Pump System with Calibration Curve" incorporated herein by reference.

For example, the positive displacement pump may be a solenoid pump, a gear pump, an annular pump, a peristaltic pump, a syringe pump, a piezo pump or any other type of positive displacement device that is designed to pump a fixed displacement for each pump cycle.

The pumps 160 and the metering devices 170 may be in communication with a dispensing nozzle 180. The dispensing nozzle 180 preferably may be a multi-flavor dispensing valve capable of mixing a number of fluids at the same time. Examples of dispensing nozzles that may be used herein are shown in commonly owned U.S. Pat. No. 7,383,966, entitled "Dispensing Nozzle" and commonly-owned U.S. Pat. No. 7,578,415, entitled "Dispensing Nozzle Assembly". U.S. Pat. No. 7,383,966 and U.S. Pat. No. 7,578,415 are incorporated herein by reference.

Figure 2:
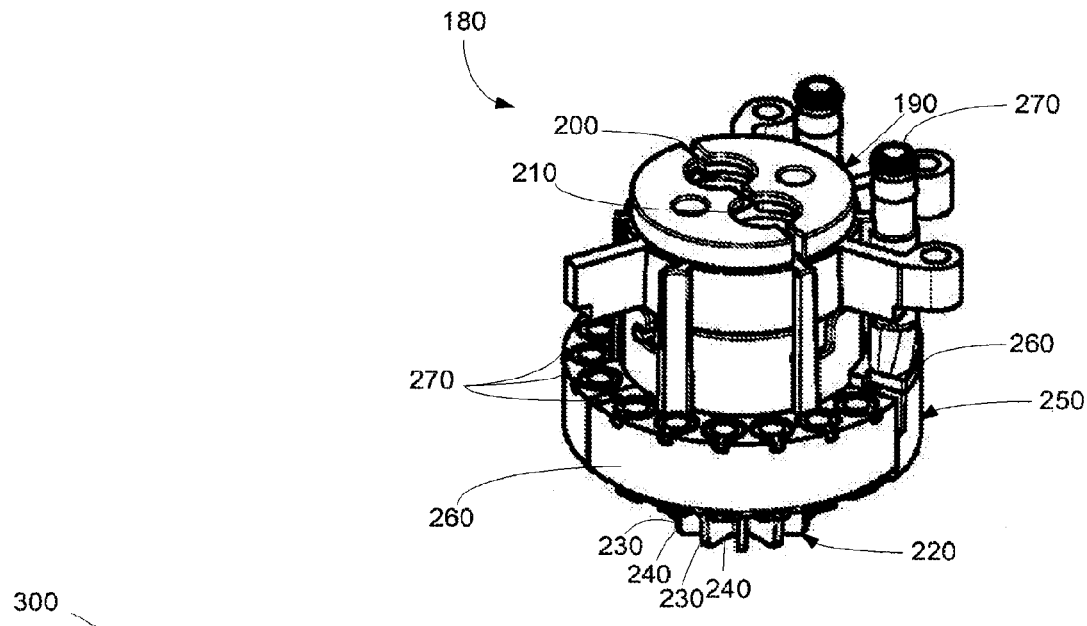
FIG. 2 is a perspective view of a dispensing nozzle assembly that may be used with the beverage dispenser of FIG. 1.

FIG. 2 shows an example of such a dispensing nozzle 180. Generally described, the dispensing nozzle includes a flow director 190 with a number of conduits extending therethrough. In this example, the flow director 190 may have a first conduit 200 and a second conduit 210 extending therethrough. The first conduit 200 may be used for water, other types of diluents, or other fluids. The second conduit 210 may be used for a macro-ingredient such as sweetened concentrate, sugar syrup, HFCS syrup, juice concentrate, or other type of fluids. Positioned beneath the flow director 190 may be a target 220. The target 220 may include a number of vertically extending fins 230 that form a number of U- or V-shaped channels 240. The water, the macro-ingredients, or other fluids may flow out of the flow director 190 and down along the channels 240 of the target 220 so as to begin mixing.

Positioned adjacent to the flow director 190 may be a tertiary flow assembly 250. The tertiary flow assembly 250 may include a number of modules 260. The modules 260 may have a number of conduits 270 extending therethrough. The conduits 270 may have differing sizes and configurations depending upon the nature of the intended flow therethrough. The modules 260 may be replaceable and interchangeable. Each of the modules 260 and the conduits 270 may be in communication with one of the micro-ingredient sources 150 or other types of fluids. The conduits 270 may be aimed towards the target 220 so as to mix the micro-ingredients or other fluid with the water, the macro-ingredients, or other fluid. Any number of micro-ingredients or other types of fluids may be used at the same time.

Figure 3:
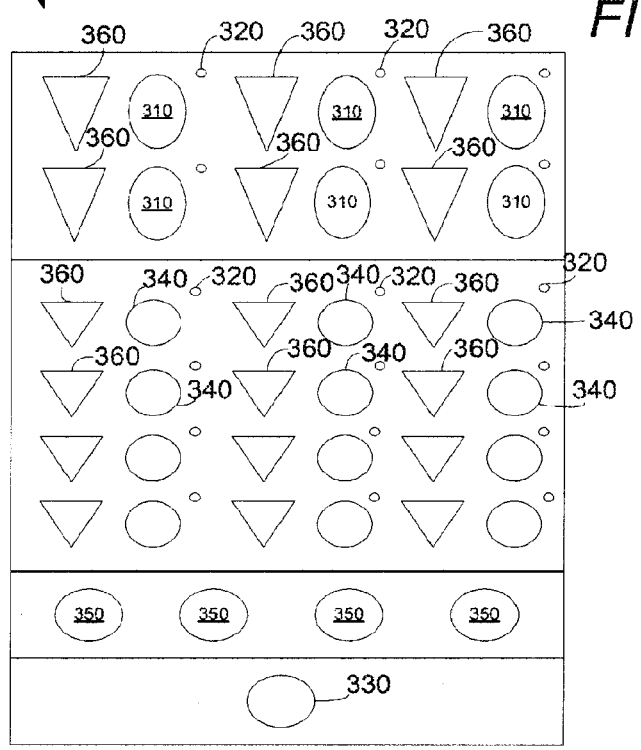
FIG. 3 is a schematic view of a user interface for use with the beverage dispenser of FIG. 1.

FIG. 3 shows an embodiment of the user interface 110, an interface 300. The interface 300 may include a set of predefined product buttons 310. Each product button 310 may represent a different base product or product component. Each product button 310 may have a use indicator 320 that may signal to a consumer that a certain product or ingredient has been selected. A pour/cancel button 330 also may be used to activate the beverage dispenser 100 for the selected beverage.

The interface 300 further may include a number of additive buttons 340. In addition to the predefined products defined by the product buttons 310, the additive buttons 340 provide for the addition of additives such as flavorings, colorings, functional attitudes, and the like as described above. Typically, the additives will not be added until about eighty percent (80%) of the minimum drink size is poured so as to guarantee that there is no overdose effect if the drink is stopped prematurely. Additives generally would not be added for top-offs as the known drink size is not guaranteed. In the event that that the user presses the "cancel" button 330, the additives will not be dispensed. The use indicator 320 may flash whenever an additive is being provided. The user interface 300 thus gives visible feedback to the consumer.

The interface 300 also may include portion buttons 350. The portion buttons 350 may be conventional "small", "medium", "large", "extra large", and the like that correspond to the predetermined beverage sizes.

The interface 300 also may include intensity indicators 360. The intensity indicators 360 may include LED's (Light Emitting Diodes) or a similar type of visual interface that shows the relative strength of the beverage. For example, different types of juices may be desired to be mixed together so as to provide a custom-blended beverage. The intensity indicator 360 also may be used to vary the amount of additives or even the nature and amount of the concentrate, sweetener, or other types of ingredients.

In addition to the interfaces described above, additional graphical interfaces may be provided. For example, nutritional information may be provided. Whenever a portion button 350 or an intensity button 360 is selected, the nutritional information that reflects the characteristics of the selected drink may be displayed. For example, the amount of calories in the beverage as mixed by the consumer may be displayed. The consumer may then have the option to change the nutritional value of the beverage as desired. The computer user interface 300 also may restrict and/or allow which and how much of various ingredients may be used.

The computer user interface 300 may provide an individual consumer with secure access by password, smart card, biometric identification, credit card, RFID, or otherwise. The user interface 300 may provide the consumer with formulations previously selected, promotions, and other types of information. The user interface 300 may restrict and/or allow which and how much of various ingredients may be used by a consumer. Consumer preferences also may be retained and used for new product development.

In addition to the graphical interface, the beverage dispenser 100 as a whole may supply dispenser statistics and troubleshooting information. For example, the delay time for the start of the pumps 160 or the metering devices 170, the times for the vent and/or flush cycles, the portion cycles, etc. may be accessed through the user interface 110, 300. This interface 110, 300 may be password or otherwise protected. The user interface 110, 300 may communicate and/or be accessed as needed with a network or other source for troubleshooting or repair and for notifications or alerts, for example, of a potential incorrect dose of ingredients.

In use, a consumer may select the desired beverage from the user interface 110. The beverage dispenser 100 thus provides the consumer with the ability to create and blend numerous types of beverages as desired. The consumer can alter the ingredients as well as the intensity of the beverage to taste. As such, the consumer can submit an entire "recipe" for a custom beverage. Alternatively, the consumer can request a "branded" beverage. For example a "Cherry Coke®" beverage sold by The Coca-Cola Company of Atlanta, Georgia is more than just a "Coca-Cola®" beverage with the addition of a shot of cherry flavoring. Rather, it is a specific branded beverage with a consistent taste. The beverage dispenser 100 thus may provide as many "branded" beverages as may be available on the market in bottles, cans, or otherwise.

The interface 110, with the control 120, then instructs the individual pumps 160 and/or the metering devices 170 to dispense the appropriate ingredients in the appropriate proportions to the dispensing nozzle 180. The mixed beverage then flows into the consumer's cup in the predetermined proportions for a given flow rate. The pumps 160 and the metering devices 170 may be pulsed on and off as desired to vary the flow rate. Such pulsing, for example, may ensure mixing of the micro-ingredients and may provide for a varied carbonation level. The beverage may be mixed at the dispensing nozzle 180 or anywhere downstream of one or more of the sources 130, 140, 150 (e.g., back room, in-line, etc.) Different flow rates and flow timing may be employed, e.g., certain fluid streams may be added early or late, certain fluid streams may be pulsed, etc.

The use of the individual pumps 160 and/or the metering devices 170 for the water source 130, the macro-ingredient sources 140, and the macro-ingredient sources 150 provides the ability to dispense the appropriate ingredients in the appropriate proportions for a given flow rate during a continuous pour. In other words, as opposed to a conventional batch operation where a predetermined amount of ingredients are combined, the beverage dispenser 100 provides for continuous mixing and flows in the correct ratios for a pour of any volume. The beverage dispenser 100 thus has applicability to conventional countertop devices, vending devices, and various types of bottling and filling devices. Although the invention is described in terms of the beverage dispenser 100, the invention is applicable to the combination of any types of ingredients, wet or dry. Commonly owned U.S. patent application Ser. No. 11/276,549, entitled "Juice Dispensing System", is specifically directed towards the use of the concepts described herein in the juice field. U.S. patent application Ser. No. 11/276,549 is incorporated herein by reference.

Referring again to FIG. 1, the beverage dispenser 100 also may include a consumer data system 400 in communication with the user interface 110 and the control device 120. The consumer data system 400 may include a communication device 410. The communication device 410 may include a video touch screen, a video screen and keyboard, or any other type of conventional input/output device. The communications device 410 may be part of the user interface 110 or a separate element.

The communications device 410 may prompt the consumer to input data on various type of biometric, health, lifestyle, and/or other types of information. Based upon the consumer's input, the control device 120 may analyze the data and may suggest a beverage or beverage ingredients that may be ameliorative, beneficial, or simply amusing the consumer in light of the data input.

Health parameters may include height, weight, blood pressure, blood glucose levels, insulin levels, cholesterol levels, bone density, heart rate, other types of metabolic information, body mass percentages, body temperatures, smoking history, pregnancy, overall medical history, etc. Lifestyle questions may include mood, intensity workouts, etc. Other types of categories may include the time of day, outside temperature, current events, team affiliations, etc. Any type of data may be requested.

Based upon the inputted data, the communications device 410 of the consumer data system 400 may suggest a beverage with various types of vitamins, minerals, herbal extracts, over-the-counter medicines, colorings, etc. A beverage with a specific amount of calories may be suggested. For example, a beverage with a "bones" package, i.e., Vitamin D and calcium; an "anti-oxidant package", i.e., Vitamins C and E and zinc; a "heart package", i.e., plant sterols and B vitamins; and many other additives or mixtures may be suggested. Once a beverage and/or the additives are selected, the appropriate micro-ingredients 150 or other elements may be dispensed via the pumps 160 and the metering devices 160 as is described above. The consumer data also may be stored and compared to the current data.

In addition to the communications device 410 as described above, the consumer data system 400 also may include one or more biometric sensors 420. The biometric sensors may include automated devices to gather the desired health data or other information. The biometric sensors 420 may include a scale, a blood pressure cuff, a breathalyzer, a blood analyzer, a hair analyzer, an EKG, etc. Any type of monitoring device may be used herein. Any number of biometric sensors 420 may be used together. The biometric sensors 420 may be in communication with the control device 120 as described above.

It should be apparent that the foregoing relates only to the preferred embodiments of the present application and that numerous changes and modifications may be made herein by one of ordinary skill in the art without departing from the general spirit and scope of the invention as defined by the following claims and the equivalents thereof.

We claim:

1. A beverage dispenser, comprising:
a biometric sensor configured to collect health data;
a control device in communication with the biometric sensor, wherein the control device receives the health data and determines a beverage recommendation based at least on the health data; and
a plurality of metering devices configured to dispense a diluent and at least one ingredient to a dispensing valve, wherein each of the at least one ingredient is based on the recommended beverage.

2. The beverage dispenser of claim 1, wherein the biometric sensor is further configured to determine parameters comprising one or more of a height, a weight, a blood pressure, a blood glucose level, a cholesterol level, an insulin level, a heart rate, a bone density, or a body temperature.

3. The beverage dispenser of claim 1, wherein the biometric sensor comprises one or more of a scale, a blood pressure cuff, a breathalyzer, a blood analyzer, a hair analyzer, or an electrocardiography device.

4. The beverage dispenser of claim 1, wherein the control device is further configured to receive environmental data, and recommend a second beverage based at least on the environmental data, wherein the environmental data comprises data associated with one or more of time of day, outdoor temperature, a current event, or a team affiliation.

5. The beverage dispenser of claim 1, wherein the recommended beverage comprises one or more of a vitamin additive, a mineral additive, an herbal extract additive, a medicine additive, a nutraceutical additive, or a coloring additive.

6. The beverage dispenser of claim 1, wherein the recommended beverage has a specific amount of calories.

7. The beverage dispenser of claim 1, further comprising a user interface configured to receive a selection of the recommended beverage.

8. The beverage dispenser of claim 1, wherein the dispensing valve is configured to dispense the recommended beverage formed from the diluent and the at least one beverage.

9. A method for dispensing a beverage, comprising:
collecting health data from one or more biometric sensors coupled to a beverage dispenser;
providing, via a control device associated with the beverage dispenser, a recommendation for a beverage based at least on the health data;
receiving a selection of the recommended beverage at a user interface associated with the beverage dispenser; and
dispensing, via a plurality of metering devices associated with the beverage dispenser, a diluent and at least one ingredient based on the recommended beverage to a dispensing valve associated with the beverage dispenser.

10. The method of claim 9, further comprising determining, via at least one of the one or more biometric sensors, parameters comprising one or more of a height, a weight, a blood pressure, a blood glucose level, a cholesterol level, an insulin level, a heart rate, a bone density, or a body temperature, wherein the one or more biometric sensors comprise one or more of a scale, a blood pressure cuff, a breathalyzer, a blood analyzer, a hair analyzer, or an electrocardiography device.

11. The method of claim 9, wherein providing the beverage recommendation comprises providing, via the control device, a recommendation for one or more of a vitamin additive, a mineral additive, an herbal extract additive, a medicine additive, a nutraceutical additive, or a coloring additive.

12. The method of claim 9, wherein the providing comprises providing, via the control device, a recommendation for a specific amount of calories.

13. The method of claim 9, further comprising dispensing, via the dispensing valve, the recommended beverage formed from the diluent and the at least one ingredient.

14. The method of claim 9, further comprising receiving one or more of environmental data or lifestyle data at the control device, and recommending a second beverage based at least on one or more of the environmental data or the lifestyle.

15. The method of claim 9, wherein the one or more biometric sensors are separate from the beverage dispenser.

16. A beverage dispenser, comprising:
   at least one ingredient source;
   a diluent source;
   a dispensing valve;
   a plurality of metering devices positioned between the at least one ingredient source, the diluent source, and the dispensing valve;
   at least one biometric sensor configured to collect health data;
   a control device in communication with the biometric sensor, wherein the control device determines a beverage recommendation based at least on the health data; and
   a user interface that presents the beverage recommendation and receives a selection of the recommended beverage,
   wherein the control device is further configured to instruct at least one of the plurality of metering devices to dispense a diluent and at least one ingredient based on the recommended beverage to the dispensing valve.

17. The beverage dispenser of claim 16, the at least one biometric sensor further configured to determine parameters comprising one or more of a height, a weight, a blood pressure, a blood glucose level, a cholesterol level, or a body temperature.

18. The beverage dispenser of claim 16, the at least one biometric sensor comprising one or more of a scale, a blood pressure cuff, a breathalyzer, a blood analyzer, a hair analyzer, or an electrocardiography device.

19. The beverage dispenser of claim 16, further comprising a consumer data system comprising one or more biometric sensors.

* * * * *

UNITED STATES PATENT AND TRADEMARK OFFICE
CERTIFICATE OF CORRECTION

PATENT NO.       : 9,434,596 B2
APPLICATION NO.  : 14/317821
DATED            : September 6, 2016
INVENTOR(S)      : Carpenter et al.

It is certified that error appears in the above-identified patent and that said Letters Patent is hereby corrected as shown below:

In the Specification

Column 1, Line 56, change "Theses" to -- These --
Column 4, Line 33, change "near by" to -- nearby --
Column 5, Line 50, change "that that" to -- that --
Column 7, Line 25, change "type" to -- types --

Signed and Sealed this
Ninth Day of May, 2017

Michelle K. Lee
*Director of the United States Patent and Trademark Office*